US011130938B2

(12) United States Patent
Mogna et al.

(10) Patent No.: US 11,130,938 B2
(45) Date of Patent: Sep. 28, 2021

(54) COMPOSITIONS COMPRISING LIVE PROBIOTIC BACTERIAL CULTURES OF *LACTOBACILLUS, BIFIDOBACTERIUM, LACTOCOCCUS, STREPTOCOCCUS,* OR *STAPHYLOCOCCUS*

(71) Applicants: Probiotical S.p.A., Novara (IT); Vera Mogna

(72) Inventors: Giovanni Mogna, Novara (IT); Gian Paolo Strozzi, Novara (IT)

(73) Assignee: Probiotical S.p.A., Novara (IT)

( * ) Notice: Subject to any disclaimer, the term of this patent is extended or adjusted under 35 U.S.C. 154(b) by 52 days.

(21) Appl. No.: 16/544,504

(22) Filed: Aug. 19, 2019

(65) Prior Publication Data

US 2020/0063220 A1  Feb. 27, 2020

Related U.S. Application Data

(63) Continuation of application No. 12/089,618, filed as application No. PCT/IT2006/000574 on Jul. 26, 2006, now Pat. No. 10,428,395.

(30) Foreign Application Priority Data

Oct. 11, 2005 (IT) .......................... MI2005A001910
Jun. 23, 2006 (IT) .......................... MI2006A001212

(51) Int. Cl.
*C12N 1/20* (2006.01)
*A23L 33/135* (2016.01)
(Continued)

(52) U.S. Cl.
CPC ............ *C12N 1/205* (2021.05); *A23L 33/135* (2016.08); *C12N 1/20* (2013.01); *C12R 2001/01* (2021.05);
(Continued)

(58) Field of Classification Search
CPC ............ A61K 2035/115; A61K 31/715; A61K 35/741; A61K 31/7004; A61K 31/7016; A61K 31/716; A61K 9/0053; A61K 31/09; A61K 31/11; A61K 31/12; A61K 31/165; A61K 31/34; A61K 31/353; A61K 31/365; A61K 31/366; A61K 31/7034; A61K 31/7048; A61K 31/706; A61K 35/74; A61K 45/06; A61K 9/19; A61K 35/745; A61K 31/702; A61K 31/733; A61K 35/744; A61K 35/747; A61K 35/39; A61K 35/742; A61K 38/46; A61K 9/0031; A61K 2300/00; A61K 31/375; A61K 31/593; A61K 31/047; A61K 31/19; A61K 31/192; A61K 31/197; A61K 31/198; A61K 38/164; A61K 2035/11; A61K 2039/54; A61K 2039/542; A61K 2039/545; A61K 2039/55; A61K 2039/57; A61K 2039/572; A61K 2039/575; A61K 2039/585; A61K 2039/70; A61K 31/59; A61K 31/739; A61K 35/60; A61K 39/005; A61K 39/02; A61K 39/0216; A61K 39/09; A61K 39/35; A61K 47/10; A61K 47/44; A61K 47/46; A61K 9/148; A61P 1/00; A61P 29/00; A61P 43/00; A61P 37/00; A61P 17/00; A61P 17/06; A61P 19/02; A61P 1/04; A61P 25/00; A61P 37/06; A61P 37/08; A61P 11/06; A61P 17/04; A61P 35/00; A61P 37/02; A61P 11/02; A61P 25/28; A61P 3/10; A61P 7/00; A61P 11/08; A61P 17/02; A61P 19/00; A61P 1/14; A61P 1/16; A61P 31/00; A61P 3/04; A61P 9/00; A61P 11/00; A61P 1/02; A61P 1/08; A61P 1/10; A61P 1/12; A61P 25/08; A61P 27/02; A61P 31/04; A61P 31/10; A61P 35/04; A61P 39/02; A61P 3/00; A61P 3/06; A61P 7/10; A61P 9/10; A61P 9/12; A61P 11/14; A61P 13/12; A61P 1/18; A61P 37/04; A61P 3/02; Y02A 50/30; Y02A 50/475; Y02A 50/481; Y02A 50/47; A23V 2002/00; A23L 33/10; A23L 33/135; A23L 33/17; A23L 33/18; A23P 10/00; A23P 10/30; C12R 1/01; C12R 1/46; C12R 1/225; C12R 1/23; C12R 1/245; C12R 1/25; C12R 1/44; C12R 2001/01; C12R 2001/225; C12R 2001/23; C12R 2001/245; C12R 2001/25; C12R 2001/44; C12R 2001/46;
(Continued)

(56) References Cited

U.S. PATENT DOCUMENTS 2,838,443 A  6/1958 Gillespie
3,891,773 A  6/1975 Kline et al.
(Continued)

FOREIGN PATENT DOCUMENTS

JP  62-257383  11/1987
JP  08-238066  9/1996
(Continued)

OTHER PUBLICATIONS

BR, PI 0617173118-7 Technical Opinion, dated Mar. 28, 2017.
(Continued)

*Primary Examiner* — Deborah K Ware
(74) *Attorney, Agent, or Firm* — One LLP

(57) ABSTRACT

The present invention provides anallergic compositions, including food products, comprising probiotic bacterial cultures including probiotic strains of *Lactobacillus, Bifidobacterium, Lactococcus, Streptococcus,* and/or *Staphylococcus.*

15 Claims, No Drawings

(51) Int. Cl.

| | |
|---|---|
| *C12R 1/225* | (2006.01) |
| *C12R 1/01* | (2006.01) |
| *C12R 1/23* | (2006.01) |
| *C12R 1/25* | (2006.01) |
| *C12R 1/44* | (2006.01) |
| *C12R 1/46* | (2006.01) |
| *C12R 1/245* | (2006.01) |

(52) U.S. Cl.
CPC .... *C12R 2001/225* (2021.05); *C12R 2001/23* (2021.05); *C12R 2001/245* (2021.05); *C12R 2001/25* (2021.05); *C12R 2001/44* (2021.05); *C12R 2001/46* (2021.05)

(58) Field of Classification Search
CPC . C12N 1/20; C12N 1/205; C12Q 1/10; C12Q 1/6827; C12Q 2600/156; G01N 2800/06; G01N 2800/065; G01N 33/6893; G01N 33/74; G01N 2800/56; G01N 33/573; G01N 2800/52; G01N 33/564; G01N 33/686; G01N 33/6869; A23C 20/02; A23C 9/1585; C07K 14/195; Y10S 436/809; Y10T 436/147777
See application file for complete search history.

(56) References Cited

U.S. PATENT DOCUMENTS

| | | | |
|---|---|---|---|
| 5,190,755 | A | 3/1993 | Molin et al. |
| 5,219,597 | A | 6/1993 | Mok et al. |
| 5,614,501 | A | 3/1997 | Richards |
| 6,087,092 | A | 7/2000 | Richards |
| 6,159,724 | A | 12/2000 | Ehret |
| 6,558,926 | B1 | 5/2003 | Demain et al. |
| 6,841,149 | B1 | 1/2005 | Spangler et al. |
| 7,179,460 | B2 | 2/2007 | Dennin et al. |
| 10,428,395 | B2 * | 10/2019 | Mogna .................. A61P 37/08 |
| 2005/0100559 | A1 | 5/2005 | Myatt et al. |
| 2005/0214270 | A1 | 9/2005 | Yamamoto et al. |
| 2009/0081167 | A1 | 3/2009 | Mogna et al. |
| 2009/0087418 | A1 | 4/2009 | Strozzi et al. |
| 2010/0040735 | A1 | 2/2010 | Fujiwara et al. |

FOREIGN PATENT DOCUMENTS

| | | | |
|---|---|---|---|
| JP | 2004-041099 | | 2/2004 |
| WO | WO 2005/010170 A2 | | 2/2005 |
| WO | WO-2005060937 A1 * | 7/2005 | ........... A61K 9/2013 |
| WO | WO 2006/042542 A2 | | 4/2006 |
| WO | WO 2006/123926 A2 | | 11/2006 |

OTHER PUBLICATIONS

WO, PCT/IT2006/000574 ISR and Written Opinion, dated Mar. 16, 2007.
Blandino, A., et al., "Cereal-based fermented foods and beverages", Food Research International, 2003, vol. 36, pp. 527-543.
Corradini, C., et al., "High-performance anion-exchange chromatography coupled with pulsed amperometric detection and capillary zone electrophoresis with indirect ultra violet detection as powerful tools to evaluate prebiotic properties of fructooligosaccharides and inulin", Journal of Chromatography A, 2004, vol. 1054, pp. 165-173.
Database WPI Week 199436, Thompson Scientific, Nisshin Flou Milling Co, Aug. 9, 1994, pp. 1-2.
De Man, J. C., et al., "A Medium for the Cultivation of Lactobacilli", J. Appl. Bact., 1960, vol. 23, vol. 1, pp. 130-135.
Lahtinen, S. J., "Probiotic viability—does it matter?", Microbial Ecology in Health & Disease, 2012, vol. 23, pp. 10-14.
Lee, Y. K., et al., Handbook of Probiotics and Prebiotics, 2009, Annex 1, pp. 4-5.
Marx, S. P., et al., "Metabolization of β-(2,6)-linked fructose-ogliosaccharides by different bifidobacterial", FEMS Microbiology Letters, 2000, vol. 182, pp. 163-169.
McKellar, R. C., et al., "Metabolism of fructo-ogliosaccharides by *Bifidobacterium* spp.", Appl Microbiol Biotechnol, 1989, vol. 31, pp. 537-541.
Molin, G., "Probiotics in foods not containing milk or milk constituents, with special reference to *Lactobacillus plantarum* 299v$^{1-3}$", Am J Clin Nutr, 2001, Supplement 73, pp. 380S-385S.
O'Leary, V. S., et al., "Utilization of Lactose, Glucose, and Galactose by a Mixed Culture of *Streptococcus thermophilus* and *Lactobacillus bulgaricus* in Milk Treated with Lactose Enzyme", Applied and Environmental Microbiology, 1976, vol. 32, No. 1, pp. 89-94.
Sh, C., et al., "Improvement of hydrolyzed protein media for the growth of lactic-acid bacteria", Database Biosis Biosciences Information Service, Philadelphia, PA, US, Korean J. Anim. Sci., 1981, vol. 23, No. 3, pp. 226-234.
Vasala, A., et al., "Efficient lactic acid production from high salt containing dairy by-products by *Lactobacillus salivarius* ssp. *salicinius* with pre-treatment by proteolytic microorganisms", Journal of Biotechnology, 2005, vol. 117, pp. 421-431.
Yamazaki, H., "Purification of Jerusalem Artichoke Fructans and their Utilisation by Bifidobacteria", J Sci Food Agric, 1994, vol. 64, pp. 461-465.

* cited by examiner

COMPOSITIONS COMPRISING LIVE PROBIOTIC BACTERIAL CULTURES OF *LACTOBACILLUS, BIFIDOBACTERIUM, LACTOCOCCUS, STREPTOCOCCUS,* OR *STAPHYLOCOCCUS*

CROSS-REFERENCE TO RELATED APPLICATIONS

This application is a continuation of U.S. patent application Ser. No. 12/089,618, filed Sep. 3, 2008, which is a national phase application of PCT Application No. PCT/IT2006/000574, filed Jul. 26, 2006, which claims the benefit of Italian Application No. MI2006A001212, filed Jun. 23, 2006, and Italian Application No. MI2005A001910, filed Oct. 11, 2005, all of which are incorporated by reference herein in their entireties and for all purposes.

DESCRIPTION

The aim of the present invention is a method for the preparation of anallergic probiotic bacterial cultures.

It is known that the human gastrointestinal (GI) tract contains a complex microbial, community, called microbiota, mainly consisting of strictly anaerobic bacteria capable of playing different actions with effects which affect the local gastrointestinal level and indirectly the general systemic level, involving almost all the organs and the host functions.

The intestinal microflora, consisting of a large variety of different species (400-500) capable to colonize both the intestinal mucosa and the particles of ingested food, is then able to strongly condition the health of the individual.

The composition of the intestinal microflora can be altered by several factors, such as the age, the physiological condition of the individual, the presence of different pathologies, the stress and above all the diet.

As a consequence of endogenous and exogenous negative factors, there is a decrease of the useful bacteria (typically bacteria belonging to the lactic acid group in the small intestine and bifidobacteria in the large intestine) and an increase of pathogenic enterobacteria, streptococci and clostridia.

The administration of specific probiotics through medicinal specialties, dietetics, integrators and above all food (so-called "functional" or "nutraceutic" foods) allows to re-equilibrate the microflora of the host, by restoring an optimal intestinal functionality.

The term "probiotic" commonly relates to living microorganisms, selected from the intestinal microflora of healthy individuals, which once administered in opportune quantities and for an adequate time, are able to colonize, also if only temporarily, the different tracts of the intestine and to impart beneficial effect to the health of the host organism.

Belonging to the probiotics are mainly some species of the genera *Lactobacillus, Bifidobacterium, Streptococcus, Pediococcus, Lactococcus, Propionibacterium, Leuconostoc* and, in a lower extent, *Saccharomyces, Bacillus* and *Enterococcus*.

Between the healthy and beneficial effects, shown by severe clinical tests carried out all over the world and induced in the consumer by the intake of probiotics there can be mentioned:
1. Stimulation of the immune system;
2. Induction of antimutagenic and antigenotoxic effects;
3. Antitumoral and antimetastatic action referring, for example, to:
    large intestine carcinoma
    breast carcinoma
    bladder cancer
4. Improvement in the nutrients absorption;
5. Decrease of the lactose intolerance symptoms;
6. Improvement of the intestinal motility due to the lowering of the pH and decrease of the constipation;
7. Decrease of the absorption of cholesterol and fats;
8. Antidiarrhoic, anti-hypertensive, anti-diabetic activities inhibiting infections of the female urogenital system;
9. Prevention activity of geriatric pathologies.

The probiotics for oral use must be characterized by the following general and functional requirements:
i) human intestinal origin; from individuals in good health conditions;
ii) bio-safety; they must not cause side effects especially in weakened or immune depressed persons;
iii) Resistance and viability; they must have such resistance features to be able to survive the gastric juice, the pancreatic and bile secretions so as to reach the ileum and the colon in an undamaged way and still perfectly viable.

The competition which begins between probiotic microorganisms and pathogenic microflora can only occur if, once ingested, the probiotic microorganisms are able to reach the intestinal tract and therefore to survive the gastric acidity and the high concentration of the bile salts. Generally, once they have reached the intestinal tract, they are said to begin through adhesion mechanisms which involve proteins and/or carbohydrates with specific adhesion functionalities to the intestinal villi.

At industrial level, the probiotics are produced in form of freeze dried bacterial culture, namely the growth of the cells in a proper medium is determined (fermentation) and next, following to concentration and purification of the biomass, the dehydration of the same is performed by freeze drying. Such process is required for allowing the bacteria to reproduce themselves in an adequate number (fermentative step) and to preserve themselves for a long time (freeze drying step).

In order that the fermentative process is successfully carried out and with adequate yields, it is necessary to provide the cells with carbon and nitrogen sources, oligo-elements and bioactivators in opportune quantities.

Traditionally, dealing with commonly said "lactic" bacteria, the selected substrates used as a nitrogenous source are serum, milk serum-proteins, hydrolyzates and casein peptones, caseinates, etc., while as a carbon source, lactose and glucose are usually employed, as they can easily be metabolized from almost all the living organisms.

In the last years, probably also because of a diet too little varied and too rich in proteins and lipids, in Europe and Western countries a sensitive increase of the number of persons suffering from allergic-type pathologies has been registered.

The immune reactions of type IV or IgE-mediated are called "allergic", during which, following to a first sensitizing contact (which can occur in any time of the life, also the intrauterine one) specific IgEs are produced with a histamine-mediated mechanism.

Such reactions can be also caused by extremely reduced doses of molecules called "allergens", with clinical consequences which can change from simple slight skin reactions to anaphylactic shock and dead.

Due to the dangerousness of these substances for some people, the European Community has adopted a rule such that in the label "the use in the production and the presence in the food" of foods belonging to the following classes (Annex III bis of the above instruction) has to be clearly shown (art. 6 sub. 10, instruction 2000/13/EC thus modified by the instruction 2003/89/EC):
gluten-containing cereals (that is wheat, rye, barley, oat, spelt, kamut or their hybridized-strains) and derived products; crustacea and crustacea-based products; eggs and eggs-based products; fish and fish-based products; peanuts and peanut-based products; soy and soy-based products; milk and milk-based products (including the lactose); fruits with shell, that is almonds (*Amigdalus communis* L.), hazelnuts (*Corylus avellana*), common walnuts (*Juglans regia*), acagiu walnuts (*Western Anacardium*), pecan walnuts [*Carya illinoiesis* (Wangenh) K Koch], Brazil walnuts (*Bertholletia excelsa*), pistachio nuts (*Pistacia vera*), Queensland walnuts (*Macadamia ternifolia*) and derived products; celery and celery-based products; mustard and mustard-based products; sesame seeds and sesame seeds-based products; sulfur dioxide and sulphites in concentrations higher than 10 mg/kg or 10 mg/l expressed as $SO_2$.

As, typically for the production of probiotics, substrates based on milk (as a nitrogenous source) and glucose (as a carbon source), which is usually originated from the starch (also wheat starch), derivatives are used, the probiotics can be considered dangerous if administered to particularly sensitive subjects, even if, at the most, they actually could contain only small traces of allergens (therefore derived from milk and/or gluten).

In case of milk, there can be individualized two causes of adverse reaction to this food; the cow's milk proteins allergy (APLV) and the lactose intolerance.

The milk, together with the egg, is the more allergising food; this feature thereof is determined by the proteinic substances contained by the same, that is mainly alfa-lactoalbumin, beta-lactoglobulin and caseins.

The allergy to the cow's milk proteins is a relatively frequent pathology in the first year of life. The symptomatology is, in the 50-70% of the cases, of a gastroenteric type, yet in the 50-70% of the cases there are skin disorders, in the 20-30% respiratory disorders and in the 5-9% systemic disorders (anaphylaxis).

The APLV tends to fade itself after the first year of life and to disappear towards the 10 years and is unusual in the adults.

An opposite course has the lactose intolerance, which is very unusual in the first year of life and very frequent in the adult, in particular in some populations (African, Asiatic, American Indian).

The milk is a fundamental food since the birth and the new-born already produces the enzyme necessary for the fission of the milk sugar, the lactose, in its simple components glucose and galactose. After the first year of life, the milk becomes a less important food and the lactase is spontaneously reduced, such that many adults become intolerant (not allergic) to the milk. The celiac disease is an enterophatic, chronic, immune-mediated inflammatory disease, risen from the ingestion of gluten, a "storage" protein naturally contained in some cereals.

This food intolerance affects genetically predisposed persons, having an immune system which responds in an abnormal way to the ingestion of proteinic fractions typical of the wheat gluten, spelt (a kind of wheat), kamut and spella (a kind of wheat), barley, rye, triticale (a cross between wheat and rye) and their derivatives. Some individuals also present intolerance to the oat proteins.

Technically the term "gluten" applies for the combination of the simple prolaminic (rich in proline), called "gliadins", and glutelinic (rich in glutamine), called "glutenins", proteins of the cereals above mentioned.

In the context of the celiac disease, the term "gluten" is often used with reference to all kinds of proteins contained in the cereals, even if between the different proteinic fractions which form the gluten, the gliadin seems to be the most detrimental.

In the people affected by the celiac disease, the assumption of gluten, also in small quantities, is capable of causing the abnormal response of the immune system: the transglutaminase, an enzyme existing in the intestinal mucosal tissue, binds to the gliadin and through deamidation transforms it in a molecule capable of activating the T cells (cells of the immune system capable of mediating all the immune responses towards the proteinic antigens), with a consequent production of anti-transglutaminase IgG and IgA and anti-endomise IgA immunoglobulins.

In a first stage, an increase of the intraepithelial intestinal activated T cells occurs, while with the progress of the disease the increase relates both to the lymphocytes and the infiltrated plasma cells of the own lamina, with a production of metalloproteinases responsible for the shortening of the villi and therefore the damage to the intestinal mucosa.

The possibility of preventing the development or treating the celiac disease does not exist so far, therefore a gluten-free diet, strictly carried out for all the lifetime is the only therapy capable of ensuring to the people affected by the celiac disease a perfect health.

The celiac persons must eliminate also the smallest traces of flour of the dangerous cereals, because the intake of gluten, also in minimal quantities, can unbridle the autoimmune response.

As the ratio of the quantity of ingested gluten to the toxic effect induced at the intestinal level has still not been defined, the term "traces" has a fundamental practical importance in the treatment of the celiac disease and implications on the food legislation plan, because it is related at the maximum limit of "acceptable" gluten (threshold) in the products suitable for the diet of the celiac person. All the skilled persons agree that a dose of 100 mg per day of gliadin, equal to 200 mg of gluten, i.e. about 3 g of bread, is sufficient to cause, in most of the celiac persons, the increase of the intestinal intraepithelial lymphocytes, a premature sign of persistent intestinal inflammation.

With reference to the minimum threshold, the few scientific works carried out so far would seem to show that the ingestion up to 10 milligrams per day of gliadin (equal to 20 parts per million of gluten) is not capable of sensitively damaging the intestinal mucosa, but can determine, in a minority of the cases, the gastroenteric symptoms occurrence.

At the international legislative level, the old standard "*Codex Standard for Gluten-Free Foods*", still in force, shows, as the maximum gluten content in the diet-therapeutic products, 0.05 of nitrogen per 100 g of dry product (with reference to the wheat starch), which corresponds to a gluten fraction equal to about 500 ppm.

However, a right and proper review of the aforesaid guide line is taking place, which seems to foresee that the gluten-free foods resulting from naturally gluten-free ingredients have not to contain more than 20 ppm of gluten, while the gluten-free foods, deriving from cereals with gluten, can have a maximum limit of 200 ppm of gluten.

In France, Great Britain and the Netherlands, waiting for the review of the aforesaid guide line, they consider, as the maximum limit for the gluten-free products, 200 ppm.

In the national ambit, the current rule seems to be more precautionary than the community and international one, in fact a limit of "20 parts per million", both for the foods manufactured with raw materials naturally free from gluten and the foods purified from such substance, is established.

The rule foresees that "if, in the composition of the food product or in that of one or more ingredients (flavourings, additives or co-adjuvants) which form the same, are present cereals containing gluten or substances deriving therefrom and/or if from the productive process a quantity of gluten can derive in the end product, analytically determined as higher than 20 parts per million, such product will have to show in the label, at the foot of the ingredients list and in a well visible way, the words "gluten-containing product"".

The complete exclusion of the gluten from the diet is not however easy to carry out, considering that cross-contamination phenomena of cereals and derivatives (starches, flours, starch flour, etc.) naturally free from gluten, already at the milling industry level, can occur.

Such products are then used by the food industry in the preparation of complex foods based on multiple technological ingredients, additives and co-adjuvants of different origin and nature.

A recent research has shown that up to 6% of the "theoretically" gluten-free products, based on the reported ingredients, actually contain over 30 mg of gliadin per 100 g of end product, equal to 600 ppm of gluten.

For the purpose of excluding a possible gluten-contamination, it is therefore necessary to consider, for each commercialized food product, not only all the ingredients used and the processing, but also all the productive chain of each single ingredient.

Therefore, there remains the need of being able to produce probiotic bacterial cultures free from allergising substances due to the use of fermentative substrates based on milk or cereals or, alternatively, due to unintentional or cross-contaminations. In fact, it is nevertheless possible that, due to cross-, unintentional and accidental contaminations, some components used in the productive process brings allergens traces.

Therefore, there remains the need of being able to provide a method for the preparation of probiotic bacterial cultures which foresees, in each step of the productive process, including the fermentation, the use of anallergic substances. In particular, it is desirable to locate and select fermentative substrates, different from milk and its derivatives and the gluten-containing cereals, which represent a good nitrogen and carbon source.

Therefore, all the sector operators agree that, so far, there remains a very strong need of providing a method for the preparation of probiotic bacterial cultures capable of using substrates alternative to those used until today and, simultaneously, capable of reducing the cross-, unintentional and accidental contaminations, should they occur.

In particular, there remains the need of providing a method for the preparation of probiotic bacterial cultures which foresees a double level of safety relating to the absence of allergising substances.

An aim of the present invention is to provide a method for the preparation of culture media capable of overcoming the limits of the known art.

Another aim of the present invention is to provide a methodology for the production of probiotic bacterial cultures safe to administer to all the population, also to the people affected by allergies.

These and other aims, which will result apparent from the following detailed description, have been attained by the Applicant, which has improved a methodology which includes a double safety level relating to the absence of allergens in the productive processes of probiotic bacterial cultures.

In particular, the Applicant has set up a production methodology in which selected anallergic fermentation substrates (anallergic raw materials) are used, capable of ensuring a proper nitrogen and carbon source to the probiotic cultures.

A method for the preparation of an anallergic probiotic bacterial cultures, a composition including said culture and the use of said culture for the preparation of so-called "functional" or "nutraceutic" foods form the subject of the present invention, having the features as defined in the appended claims.

In an embodiment of the invention, the strains of said bacterial culture belong to the genera: *Lactobacillus, Bifidobacterium, Streptococcus, Pediococcus, Lactococcus, Propionibacterium, Bacillus, Saccharomyces, Enterococcus, Leuconostoc.*

Preferably, of the genus *Lactobacillus*, the following species have found use: *L. pentosus, L. plantarum, L. casei, L. casei* ssp. *paracasei, L. casei* ssp. *rhamnosus, L. acidophilus, L. delbrueckii* ssp. *bulgaricus, L. fermentum, L. gasseri.*

Examples of used strains of said species are reported in the enclosed Table 1. Preferably, of the genus *Bifidobacterium*, the following species have found use: *B. longum. B. breve, B. lactis, B. adolescentis* and *B. pseudocatenulatum.*

Examples of used strains of said species are reported in the enclosed Table 1. Preferably, of the genus *Lactococcus* the following species have found use: *L. lactis* and *L. lactis* ssp. *Lactis.*

Examples of used strains of said species are reported in the enclosed Table 1. Preferably, of the genus *Streptococcus* the following species have found use: *S. thermophilus.*

Examples of used strains of said species are reported in the enclosed Table 1.

In a particularly preferred embodiment of the invention, the bacteria of said bacterial culture are selected from the group including the probiotic bacterial strains reported in the enclosed Table 1.

The Applicant has found useful to select and employ particular anallergic raw materials. In particular, the Applicant has found, as a nitrogen source, peptones and/or proteinic hydrolyzates of vegetal and/or animal origin, naturally free from gluten and allergens of milky origin and, as a carbon source, glucose and/or other mono- or disaccharides derived from the hydrolysis of more complex polysaccharides typical of vegetal species naturally free from gluten and allergens of milky origin.

The peptones of vegetal origin are selected from the group including: rice, potato, maize, chestnuts, tapioca, manioca, pea, broad beans and their mixtures however capable of promoting the fermentation bacterial growth, but without producing allergens, either of milky nor gluten types.

In a first preferred embodiment, the method subject of the present invention foresees the use, as a nitrogen source, of one or more peptones and/or anallergic proteinic hydrolyzates and, as a carbon source, glucose and/or other mono- or disaccharides derived from hydrolysis of complex polysaccharide (anallergic raw materials).

In a second preferred embodiment, the method subject of the present invention foresees a pre-treatment of the raw materials with enzymes suitable for the removal of traces, if any, of allergens deriving from cross-contamination occurred along the productive and/or distributive chain.

In the context of the present invention, the culture substrate is an anallergic culture substrate of vegetal and/or animal origin, naturally free from gluten, allergens or milky origin and all the substances belonging to the list of the annex III bis of the instructions (anallergic raw materials) above mentioned. The use of anallergic raw materials above mentioned allows to obtain certifiable probiotics for the use in allergic persons, as the non-use of substances belonging to the list of the annex III bis of the aforesaid community instructions and the use of ingredients certified from the supplier as free from such substances can be assured.

Then, by virtue of the fact that the absence of any chemical substances in a given sample is not scientifically demonstrable, but one can simply determine that the quantity possibly existing is lower than the detection limit of the analytical method used (even if the more sensitive and refined method known in the art was used), also the use of an enzymatic pre-treatment results to be a source of an additional guarantee.

By mere way of example, some anallergic formulations of medium for the growth of probiotic bacterial cultures are reported below.

The components of a culture medium must bring nitrogen sources (in this case the peptones and/or proteinic hydrolyzates), carbon sources (in this case, the glucose and/or other mono- or disaccharides derived from hydrolysis of complex polysaccharides), growth bioactivators and vitamins (in this case from yeast extract) and mineral salts.

For example, a culture medium can contain:
glucose preferably selected from: maize starch, potato, beet sucrose or cane sucrose;
peptone preferably selected from: rice, potato, maize, chestnut, tapioca, maniocak pea, broad beans, bean or generally legumes and their mixtures;
peptone preferably selected from: meat;
yeast extract; mineral salts (such as, by mere way of example: acetates, carbonates, phosphates, hydrogen phosphates, chlorides, citrates, sulfates and others); builder (if necessary, such as: Tween, lecithins and other) and drinking water.

One of the formulation suitable for the growth of strains of the *Lactobacillus* and *Bifidobacterium* genera could preferably include the following ingredients:

| | |
|---|---|
| glucose (from the sources above listed) | 10-100 g/l |
| rice peptone | 10-50 g/l |
| meat peptone | 10-50 g/l |
| yeast extract | 2-20 g/l |
| mineral salts | 1-10 g/l |
| builders | 0-5 ml/l |
| drinking water | q.s. to the desired volume |

A preferred example of a medium for anallergic probiotic bacterial cultures could be the following:

| | |
|---|---|
| glucose (from maize starch) | 20 g/l rice |
| peptone | 10 g/l |
| meat peptone | 10 g/l |
| yeast extract | 5 g/l |
| sodium acetate | 5 g/l |
| citrate ammonium | 2 g/l |
| dibasic potassium phosphate | 2 g/l |
| magnesium sulfate | 0.1 g/l |
| manganese sulfate | 0.05 g/l |
| tween 80 | 1 ml/l |
| drinking water | q.s. to the desired volume |

The fermentation is carried out according to the teachings known to the skilled in the art and under the experimental conditions of common use.

The Applicant has verify the presence, or not, of allergen traces on a probiotic culture grown on raw materials subject of the present invention.

For example, in case of milk-derived allergens, the research by analytical way of β-lactoglobulin and lactose on the end products, with confirmed specific and sensitive methodologies (analysis with ELISA kit specific for the β-lactoglobulin of the type "Bovine β-lactoglubilins ELISA quantitation kit—Bethyl Laboratories", with a threshold limit of 0.05 ppm and analysis with chemoenzymatic kit and UV-vis detection for the lactose of the type "Lactose/D-glucose—Boehringer Mannheim", cod. 10986119, with a threshold limit of 7 ppm) gives a negative result and, therefore, these substances, if any, should certainly be under the detection threshold.

At the same time, the gluten research carried out with the more refined and, so far, more sensitive confirmed methodology (ELISA RIDASCREEN® Gliadin kit—R-Biopharm A, Darmstadt, Germany, with a sensitivity equal to 3 ppm) allows to confirm the absence of gluten. It follows that, even if the gluten were present, its concentration should be in any case under the detection threshold, namely lower than 3 ppm.

The enzymatic pre-treatment on the raw materials, to be carried out or not as a function of the requirements, is able to hydrolize milk and derivatives traces and gluten and derivatives accidentally existing in the culture medium.

Such treatment imparts the highest safety standard for a use also suitable to allergic and particularly sensitive persons.

This manufacturing strategy is suitable for the probiotics production with an anallergic safety degree called DSS—Double Safety System.

The enzymatic pre-treatment foresees the use of at least a proteolytic enzyme and/or the use of at least a glycosidase enzyme.

In the context of the present invention, the proteolytic enzyme is able to perform a proteolysis. The proteolytic enzyme is selected from the group including the proteases and/or the peptidases. The proteases and the peptidases are selected from the group including: trypsin, chymotrypsin, pancreatin, pepsin, papain and bromelain. Preferably, the proteases and the peptidases are selected between pepsin and/or bromelain. In the context of the present invention, the glycosidase enzyme is able to perform a hydrolityc cleavage of a glycoside. The glycosidase enzyme is selected from the group including: alfa-glucosidase and beta-glucosidase, alfa-galactosidase and beta-galactosidase.

Advantageously, the enzymatic treatment of the raw materials forming the growth broth for the probiotics is carried out with proteases (alcalases and bromelain) and with the glycosidases.

The glycosidases are selected from the group including: lactase (or β-galactosidase). In a preferred embodiment, the pre-treatment of the raw materials foresees the use in a sequence including three enzymes: alcalase, lactase and bromelain.

In a preferred embodiment, the selection of the enzymes and their sequence is the following:
alcalase, which practically hydrolyzes all the proteins and particularly those of the milk;
lactase, which hydrolyzes the lactose;
bromelain, which hydrolyzes the gluten.

The sequence shown is a function of the optimal hydrolysis pH in a gradient from basic to acid; in this way, the medium preserves the nutritional properties. The alcalase, active towards the β-lactoglobulin, the α-lactaalbumin and the caseins, allows to eliminate allergenic residuals, if any, deriving from fortuitous and unintentional cross-contaminations with milk derivatives.

Such treatment foresees the addition to the raw materials dissolved in water of a quantity of enzyme varying from 0.0025 and 0.0500 g/l, corresponding to 0.001-0.020 AU/l (Anson Units per Liter).

The solution is then brought to a temperature between 45 and 55° C. for 15-60 minutes, with a pH between 7 and 8; preferably, a controlled pH of 7.50±0.20.

The lactase, also known as β-galactosidase, is charged to the hydrolysis of the glycoside bond between glucose and galactose in the lactose disaccharide.

The treatment with lactase is carried out following to the hydrolysis with proteins alcalase after having brought the pH of the culture broth to a value between 6 and 7; preferably, a value of 6.50±0.20 with organic acids (preferably lactic acid) by adding 250-2.000 NLU/l (Neutral Lactase Units per Liter), corresponding to 0.05-0.40 ml of an enzyme solution titrated at 5.000 NLU/g.

The solution is maintained at 37±5° C. for a varying period of 2-6 hours. Finally, the bromelain is a proteolytic enzyme naturally contained in the pineapple, capable of effectively hydrolysing the gliadin in fragments not recognized by the immune system and therefore non allergenic.

The treatment is carried out by adding the fermentation medium with the enzyme to the amount of 0.005-0.010 g/l (equal to 110-220 GDU/l, Gelatin Digesting Units per Liter), after correction of the pH to values of 5.0-6.0 with organic acids (preferably lactic acid). The working temperature must be maintained at 37±5° C. for a time between 1 and 6 hours.

Following to the three enzymatic treatments, it is necessary to restore the pH at the optimal value for the fermentation of the single strains (preferably with 5N NaOH in order to basify, or with acid lactic in order to acidify).

Next, a heat treatment for the purification of the medium is carried out (performed at temperatures between 90 and 145° C. for times varying from few seconds to 45 minutes), which will however denature and inactivate the added enzymes, without further risks for the end product and their intended people deriving from residuals of the enzyme used.

A typical industrial production design therefore foresees the following steps:
a. selection of the anallergic raw materials
b. dissolution of the raw materials in water
c. correction of the pH and temperature to proper values for the use of the proteolytic enzyme, preferably alcalase
d. addition of the enzyme and its action for the required time
e. correction of the pH and the temperature to proper values for the use of the glycolytic enzyme, preferably lactase
f. addition of the enzyme and its action for the required time
g. correction of the pH and the temperature to proper values for the use of the proteolytic enzyme, preferably bromelain
h. addition of the enzyme and its action for the required time
i. correction of the pH up to values suitable for the fermentation
j. purification through pasteurisation and/or sterilization of the culture medium.
k. cooling at the inoculum temperature typical of the probiotic strain under production (37±2° C.).
l. inoculum of the strain.
m. fermentation
n. separation of the biomass and crioprotection
o. freeze drying.

The present invention allows then to produce anallergic probiotic strains and in particular with absolute absence of allergens, more preferably of milk and gluten derivatives, with a wide safety of use for all the populations classes.

Advantageously, the anallergic probiotic bacterial cultures prepared according to the teachings of the present invention can be effectively used for the preparation of pharmaceutical formulations.

In view of the high number of persons allergic to the milk (3-5% of the population with an age below 2 years) and the celiac persons (1% of the total population) it is useful to try to develop probiotic bacteria which can be administered also to this classes of population.

The present invention is then useful:
to the consumers, for which the transparency in the labelling is fundamental;
to the producers, which in this way can rely on a product with a total guarantee of its anallergic properties, therefore proposable to the whole purchasing population.

TABLE 1

| | | |
|---|---|---|
| 1 | Streptococcus thermophilus | LMG P-18383 |
| 2 | Streptococcus thermophilus | LMG P-18384 |
| 3 | Lactobacillus pentosus | LMG P-21019 |
| 4 | Lactobacillus plantarum | LMG P-21020 |
| 5 | Lactobacillus plantarum | LMG P-21021 |
| 6 | Lactobacillus plantarum | LMG P-21022 |
| 7 | Lactobacillus plantarum | LMG P-21023 |
| 8 | Lactobacillus casei ssp. paracasei | LMG P-21380 |
| 9 | Lactobacillus acidophilus | LMG P-21381 |
| 10 | Bifidobacterium longum | LMG P-21382 |
| 11 | Bifidobacterium breve | LMG P-21383 |
| 12 | Bifidobacterium lactis | LMG P-21384 |
| 13 | Lactobacillus plantarum | LMG P-21385 |
| 14 | Lactococcus lactis ssp. lactis | LMG P-21387 |
| 15 | Lactococcus lactis ssp. lactis | LMG P-21388 |
| 16 | Lactobacillus plantarum | LMG P-21389 |
| 17 | Streptococcus thermophilus | DSM 16506 |
| 18 | Streptococcus thermophilus | DSM 16507 |
| 19 | Bifidobacterium longum | DSM 16603 |
| 20 | Bifidobacterium breve | DSM 16604 |
| 21 | Lactobacillus casei ssp. rhamnosus | DSM 16605 |
| 22 | Lactobacillus delbrueckii ssp. bulgaricus | DSM 16606 |
| 23 | Lactobacillus delbrueckii ssp. bulgaricus | DSM 16607 |
| 24 | Streptococcus thermophilus | DSM 16590 |
| 25 | Streptococcus thermophilus | DSM 16591 |
| 26 | Streptococcus thermophilus | DSM 16592 |
| 27 | Streptococcus thermophilus | DSM 16593 |
| 28 | Bifidobacterium adolescentis | DSM 16594 |
| 29 | Bifidobacterium adolescentis | DSM 16595 |
| 30 | Bifidobacterium breve | DSM 16596 |
| 31 | Bifidobacterium pseudocatenulatum | DSM 16597 |
| 32 | Bifidobacterium pseudocatenulatum | DSM 16598 |
| 33 | Staphylococcus xylosus | DSM 17102 |
| 34 | Bifidobacterium adolescentis | DSM 17103 |
| 35 | Lactobacillus plantarum | DSM 17104 |
| 36 | Streptococcus thermophilus | DSM 17843 |
| 37 | Streptococcus thermophilus | DSM 17844 |
| 38 | Streptococcus thermophilus | DSM 17845 |
| 39 | Lactobacillus fermentum | DSM 18295 |
| 40 | Lactobacillus fermentum | DSM 18296 |
| 41 | Lactobacillus fermentum | DSM 18297 |
| 42 | Lactobacillus fermentum | DSM 18298 |
| 43 | Lactobacillus gasseri | DSM 18299 |
| 44 | Lactobacillus gasseri | DSM 18300 |
| 45 | Lactobacillus gasseri | DSM 18301 |
| 46 | Lactobacillus gasseri | DSM 18302 |
| 47 | Bifidobacterium adolescentis | DSM 18350 |
| 48 | Bifidobacterium adolescentis | DSM 18351 |
| 49 | Bifidobacterium adolescentis | DSM 18352 |
| 50 | Bifidobacterium catenulatum | DSM 18353. |

The enclosed Table 1 identifies strains deposited at the BCCM/LMG Bacteria Collection of Gent, Belgium and at the DSMZ—Deutsche Sammlung von Mikroorganismen and Zellkulturen GmbH, Inhoffenstrasse 7 B, 38124 Braunschweig, GERMANY; the deposits are in accordance with the Budapest Treaty.

The invention claimed is:

1. A live probiotic food product or a live probiotic pharmaceutical formulation comprising:
   (a) a substrate comprising less than 3 ppm gluten, less than 7 ppm lactose, and less than 0.05 ppm beta-globulins; and
   (b) live probiotic bacteria selected from the group consisting of:

| | | |
|---|---|---|
| 1 | *Streptococcus thermophilus* | LMG P-18383 |
| 2 | *Streptococcus thermophilus* | LMG P-18384 |
| 3 | *Lactobacillus pentosus* | LMG P-21019 |
| 4 | *Lactobacillus plantarum* | LMG P-21020 |
| 5 | *Lactobacillus plantarum* | LMG P-21021 |
| 6 | *Lactobacillus plantarum* | LMG P-21022 |
| 7 | *Lactobacillus plantarum* | LMG P-21023 |
| 8 | *Lactobacillus casei* ssp. *paracasei* | LMG P-21380 |
| 9 | *Bifidobacterium longum* | LMG P-21382 |
| 10 | *Bifidobacterium breve* | LMG P-21383 |
| 11 | *Bifidobacterium lactis* | LMG P-21384 |
| 12 | *Lactobacillus plantarum* | LMG P-21385 |
| 13 | *Lactococcus lactis* ssp. *lactis* | LMG P-21387 |
| 14 | *Lactococcus lactis* ssp. *lactis* | LMG P-21388 |
| 15 | *Lactobacillus plantarum* | LMG P-21389 |
| 16 | *Streptococcus thermophilus* | DSM 16506 |
| 17 | *Streptococcus thermophilus* | DSM 16507 |
| 18 | *Bifidobacterium longum* | DSM 16603 |
| 19 | *Bifidobacterium breve* | DSM 16604 |
| 20 | *Lactobacillus casei* ssp. *rhamnosus* | DSM 16605 |
| 21 | *Lactobacillus delbrueckii* ssp. *bulgaricus* | DSM 16606 |
| 22 | *Lactobacillus delbrueckii* ssp. *bulgaricus* | DSM 16607 |
| 23 | *Streptococcus thermophilus* | DSM 16590 |
| 24 | *Streptococcus thermophilus* | DSM 16591 |
| 25 | *Streptococcus thermophilus* | DSM 16592 |
| 26 | *Streptococcus thermophilus* | DSM 16593 |
| 27 | *Bifidobacterium adolescentis* | DSM 16594 |
| 28 | *Bifidobacterium adolescentis* | DSM 16595 |
| 29 | *Bifidobacterium breve* | DSM 16596 |
| 30 | *Bifidobacterium pseudocatenulatum* | DSM 16597 |
| 31 | *Bifidobacterium pseudocatenulatum* | DSM 16598 |
| 32 | *Staphylococcus xylosus* | DSM 17102 |
| 33 | *Bifidobacterium adolescentis* | DSM 17103 |
| 34 | *Lactobacillus plantarum* | DSM 17104 |
| 35 | *Streptococcus thermophilus* | DSM 17843 |
| 36 | *Streptococcus thermophilus* | DSM 17844 |
| 37 | *Streptococcus thermophilus* | DSM 17845 |
| 38 | *Lactobacillus fermentum* | DSM 18295 |
| 39 | *Lactobacillus fermentum* | DSM 18296 |
| 40 | *Lactobacillus fermentum* | DSM 18297 |
| 41 | *Lactobacillus fermentum* | DSM 18298 |
| 42 | *Lactobacillus gasseri* | DSM 18299 |
| 43 | *Lactobacillus gasseri* | DSM 18300 |
| 44 | *Lactobacillus gasseri* | DSM 18301 |
| 45 | *Lactobacillus gasseri* | DSM 18302 |
| 46 | *Bifidobacterium adolescentis* | DSM 18350 |
| 47 | *Bifidobacterium adolescentis* | DSM 18351 |
| 48 | *Bifidobacterium adolescentis* | DSM 18352 and |
| 49 | *Bifidobacterium catenulatum* | DSM 18353. |

2. The food product or pharmaceutical formation of claim 1, wherein the substrate further comprises a mono- or disaccharide.

3. The food product or pharmaceutical formation of claim 2, wherein the mono- or disaccharide is glucose derived from maize starch, potato starch, beet sucrose, or cane sucrose.

4. The food product or pharmaceutical formation of claim 2, wherein the mono- or disaccharide is derived from complex polysaccharide hydrolysis.

5. The food product or pharmaceutical formation of claim 1, wherein the food product or pharmaceutical formation is freeze-dried.

6. The food product or pharmaceutical formation of claim 1, wherein the food product or pharmaceutical formation is prepared by a method comprising:
   (i) providing a fermentative substrate containing sulfur dioxide and sulfites at concentrations of not more than 10 mg/kg or 10 mg/litre expressed as $SO_2$;
   (ii) adding to the fermentative substrate provided in step (i) an exogenous meat peptone or an exogenous vegetal peptone selected from the group consisting of rice, potato, maize, chestnuts, tapioca, manioca, pea, fava beans, and mixtures thereof;
   (iii) fermenting one or more live probiotic bacteria in the fermentative substrate of step (ii) to yield a probiotic bacterial culture containing less than 3 ppm gluten, less than 7 ppm lactose, and less than 0.05 ppm beta-lactoglobulins, and
   (iv) preparing a live probiotic food product or live probiotic pharmaceutical formulation comprising said probiotic bacterial culture.

7. The food product or pharmaceutical formation of claim 6, wherein the fermentative substrate comprises (x) glucose derived from maize starch, potato starch, beet sucrose, or cane sucrose, or (y) mono- and disaccharides derived from complex polysaccharide hydrolysis.

8. The food product or pharmaceutical formation of claim 6, wherein said live probiotic food product or live probiotic pharmaceutical formulation obtained in step (iv) is freeze dried.

9. The food product or pharmaceutical formation of claim 1, wherein the food product or pharmaceutical formation is prepared by a method comprising:
   (i) preparing a fermentative substrate comprising an exogenous meat peptone or an exogenous vegetal peptone selected from the group consisting of rice, potato, maize, chestnuts, tapioca, manioca, pea, fava beans, and mixtures thereof,
   (ii) subjecting the fermentative substrate to an enzymatic treatment using a proteolytic enzyme, a glycoside enzyme, or both to obtain a fermentative substrate containing sulfur dioxide and sulfites at concentrations of not more than 10 mg/kg or 10 mg/litre expressed as $SO_2$, wherein the proteolytic enzyme is selected from the group consisting of trypsin, chymotrypsin, pancreatin, pepsin, papain, and bromelain, and wherein the glycoside enzyme is selected from the group consisting of alpha-glucosidase and beta-glucosidase,
   (iii) fermenting one or more live probiotic bacteria in the fermentative substrate to yield a probiotic bacterial culture containing less than 3 ppm gluten, less than 7 ppm lactose, and less than 0.05 ppm beta-lactoglobulins, and
   (iv) preparing a live probiotic food product or live probiotic pharmaceutical formulation comprising the probiotic bacterial culture obtained in step (iii),
   wherein the fermentative substrate, and the live probiotic food product or live probiotic pharmaceutical formulation are each substantially free of gluten and milk-derived allergens.

10. The food product or pharmaceutical formation of claim 9, wherein said enzymatic treatment comprises treating the fermentative substrate with (a) bromelain, and (b) beta-galactosidase.

11. The food product or pharmaceutical formation of claim 9, wherein said enzymatic treatment comprises treating the fermentative substrate with bromelain.

12. The food product or pharmaceutical formation of claim 11, wherein
   (x) the fermentative substrate is treated with alcalase at 45° C.-55° C., pH 7-8, for 15-60 minutes,
   (y) the fermentative substrate is treated with lactase at 30° C.-40° C., pH 6-7, for 2-6 hours, and
   (z) the fermentative substrate is treated with bromelain at 30° C.-40° C., pH 5-6, for 1-6 hours.

13. The food product or pharmaceutical formation of claim 9 wherein, following the enzymatic treatment,
   (x) the fermentative substrate pH is adjusted to a value suitable for culturing said probiotic bacteria; and
   (y) the fermentative substrate is heated to a temperature of 90° C.-145° C. for a time sufficient to inactivate enzymes used in the enzymatic treatment.

14. The food product or pharmaceutical formation of claim 9, wherein the fermentative substrate comprises (x) glucose derived from maize starch, potato starch, beet sucrose, or cane sucrose, (y) a meat peptone, and (z) a vegetal peptone selected from the group consisting of: rice, potato, maize, chestnuts, tapioca, manioca, pea, fava beans, and mixtures thereof.

15. The food product or pharmaceutical formation of claim 9, wherein said live probiotic food product or live probiotic pharmaceutical formulation obtained in step (iv) is freeze dried.

\* \* \* \* \*

UNITED STATES PATENT AND TRADEMARK OFFICE
CERTIFICATE OF CORRECTION

Page 1 of 1

PATENT NO. : 11,130,938 B2
APPLICATION NO. : 16/544504
DATED : September 28, 2021
INVENTOR(S) : Giovanni Mogna and Gian Paolo Strozzi It is certified that error appears in the above-identified patent and that said Letters Patent is hereby corrected as shown below:

On the Title Page

Under Applicants, Item (71), please remove Vera Mogna.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*